United States Patent
Brandner

(10) Patent No.: US 10,548,323 B2
(45) Date of Patent: Feb. 4, 2020

(54) METHOD OF FIGHTING SURFACE MICROORGANISMS

(71) Applicant: BMB Gebaeudehygiene GmbH, Dross (AT)

(72) Inventor: Gerhard Brandner, Dross (AT)

(73) Assignee: BMB GEBAEUDEHYGIENE GMBH, Dross (AT)

( * ) Notice: Subject to any disclaimer, the term of this patent is extended or adjusted under 35 U.S.C. 154(b) by 144 days.

(21) Appl. No.: 15/302,126

(22) PCT Filed: Apr. 8, 2015

(86) PCT No.: PCT/AT2015/050090
§ 371 (c)(1),
(2) Date: Oct. 15, 2016

(87) PCT Pub. No.: WO2015/157786
PCT Pub. Date: Oct. 22, 2015

(65) Prior Publication Data
US 2017/0181436 A1    Jun. 29, 2017

(30) Foreign Application Priority Data
Apr. 15, 2014 (AT) .................... 50280/2014

(51) Int. Cl.
| | |
|---|---|
| *A01N 59/08* | (2006.01) |
| *A01N 59/00* | (2006.01) |
| *A01N 37/36* | (2006.01) |
| *A01N 47/44* | (2006.01) |
| *C11D 3/395* | (2006.01) |
| *A01N 37/44* | (2006.01) |
| *C11D 11/00* | (2006.01) |
| *C11D 1/62* | (2006.01) |
| *C11D 3/39* | (2006.01) |
| *A01N 25/30* | (2006.01) |
| *A01N 33/12* | (2006.01) |
| *C11D 3/20* | (2006.01) |

(52) U.S. Cl.
CPC ............ *A01N 59/08* (2013.01); *A01N 25/30* (2013.01); *A01N 33/12* (2013.01); *A01N 37/36* (2013.01); *A01N 37/44* (2013.01); *A01N 47/44* (2013.01); *A01N 59/00* (2013.01); *C11D 1/62* (2013.01); *C11D 3/2086* (2013.01); *C11D 3/3942* (2013.01); *C11D 3/3953* (2013.01); *C11D 11/0052* (2013.01); *C11D 11/0058* (2013.01)

(58) Field of Classification Search
CPC ....................................................... A01N 59/08
See application file for complete search history.

(56) References Cited

U.S. PATENT DOCUMENTS

| | | | |
|---|---|---|---|
| 6,184,195 B1 * | 2/2001 | Cheung ................. | A01N 25/02 510/245 |
| 6,908,628 B2 | 6/2005 | Herruzo Cabrera | |
| 2005/0282722 A1 | 12/2005 | McReynolds | |
| 2010/0093595 A1 * | 4/2010 | Holzhauer ............... | C11D 1/83 510/342 |
| 2012/0156377 A1 * | 6/2012 | Veith .................... | C11D 3/3707 427/331 |
| 2012/0279522 A1 * | 11/2012 | Varrin, Jr. ................ | C02F 5/12 134/22.13 |

FOREIGN PATENT DOCUMENTS

| | | |
|---|---|---|
| JP | 2012250959 B | 12/2012 |
| WO | 2005075350 A | 8/2005 |
| WO | 2008116509 A | 10/2008 |

* cited by examiner

*Primary Examiner* — Adam C Milligan
*Assistant Examiner* — Sarah Alawadi
(74) *Attorney, Agent, or Firm* — Andrew Wilford

(57) ABSTRACT

The invention relates to a method for fighting mold, algae, and other microorganisms on various wall, floor, or ceiling surfaces infested with said organisms, and on masonry in general. The method comprises the following steps carried out consecutively: applying a first solution to the infested surface, wherein the first solution contains at least one surfactant compound; applying at least once a second solution that was basified by means of caustic soda to the infested surface, wherein the solution contains at least one hypochlorite compound; applying a third solution to the infested surface, wherein the solution contains at least hydrogen peroxide and lactic acid as active substances, and wherein the application of the third solution is continued until the foam formation on the infested surface has ended; applying a fourth solution to the infested surface, wherein the solution contains at least one quaternary ammonium compound.

6 Claims, No Drawings

METHOD OF FIGHTING SURFACE MICROORGANISMS

CROSS REFERENCE TO RELATED APPLICATIONS

This application is the US-national stage of PCT application PCT/AT2015/050090 filed 8 Apr. 2015 and claiming the priority of Austrian patent application A50280/2014 itself filed 15 Apr. 2014.

FIELD OF THE INVENTION

The invention relates to a method of fighting mold, algae and other microorganisms on various wall, floor or ceiling surfaces infested therewith, and on masonry in general.

STATE OF THE ART

Surface mold is a widespread problem in residential and working areas in buildings, but also in storage rooms, cellars or on external facades, terraces and other similar areas. Several methods based on acids, alcohols, oxidizing agents and alkalis provide short-term results, but after a few months there are often repeated infestations of mold, or the applied substance is highly aggressive, meaning that their application, particularly in living spaces, is only possible to a limited extent or is associated with certain other health risks due to the chemicals used.

Generally, in treatment methods used in the prior art, individual substances in a solution or a mixture of various substances is applied to the affected areas. However, individual substances alone are often not very effective, and mixtures often take their full effect when they are mixed together in their respective containers due to the individual substances reacting with each other, meaning that they do not have a sufficiently strong effect on the affected areas or on the masonry.

In addition, one thing that is common to all known methods in prior art is that the applied solutions only kill the organisms on the surface and disinfect the affected area. As yet, completely removing the organic material from the affected surface can only be achieved by chipping off the wall surface, which has considerably higher costs associated with it. Reconstructing the affected surface without completely replacing the substrate is as yet practically unknown.

OBJECT OF THE INVENTION

The object of this invention is therefore to eliminate the drawbacks outlined above and provide a method that permanently and effectively removes mold, algae and other microorganisms from infested wall, floor and ceiling surfaces, working not only on the surface but also deep into the affected areas, and that uses only substances that do not leave behind any toxic residue or degradation products, meaning that the method also is also particularly usable in living spaces or eating areas.

SUMMARY AND DESCRIPTION OF THE INVENTION

This object is achieved by the invention with a method that comprises the following steps of sequentially:
  applying to the affected surface a first solution that contains at least one surfactant compound,
  applying to the affected surface a second solution that has been made alkaline using sodium hydroxide on the affected surface and that contains at least one hypochlorite compound,
  applying to the affected surface a third solution that contains at least hydrogen peroxide and lactic acid as active substances and continuing application of the third solution for as long as necessary until foaming on the affected surface has ended,
  applying to the affected surface a fourth solution that contains at least one quaternary ammonium compound.

Within the scope of this application, the term "fighting" does not just refer to killing off undesirable organisms, but also breaking up any potential biofilms and, as far as possible, completely removing the organic material from the affected, mostly porous surface.

For the first step of the method, a first solution is used that contains at least one surfactant compound. Among other substances, the following groups can be considered as surfactant compounds: linear alkylbenzene sulfonates, alkylpolyglycosides, esterquats, fatty alcohol ethoxylates, fatty alcohol sulphates, fatty alcohol ether sulphates.

The first solution should primarily be at a neutral or preferably slightly alkaline pH (pH of 6-8). The first solution "opens" that the pores of the affected surface and the capillary action of the surface is increased, meaning that in the later stages of the method, the mold mycelium can also be wetted with the subsequent solutions deep within of the respective surface. Since wall surfaces affected by mold are often surfaces that already have an existing damp problem anyway, in cases where the wall's capillary action is already present anyway, it is increased even further by the addition of the surfactant solution and the surface begins to in effect "suck." It is necessary to carry out this step before applying the second solution in order to achieve greater penetration and enable the second solution applied afterward to reach a depth of several centimeters, depending on the substrate.

The second solution applied afterward is then drawn into the wall after it has been applied and acts as a biocide, destroying the microorganisms and organic material with the appropriate depth of penetration. In addition, the second solution leads to a cold bleaching of the black or green discoloration that is caused by the mold or algae. In this step, the applied hypochlorite is partially converted to chlorite, chlorate and perchlorate due to the increase in the pH of the prepared surface. The second step of the method can be repeated several times if necessary, depending on the surface.

During the subsequent application of the third solution, several chemical reactions take place in the masonry. When the lactic acid reacts with the active residual chlorine from the previously applied second solution, minimal amounts of chlorine gas are released. This reaction competes with the other chemical reactions between the residual chlorine and the hydrogen peroxide. In a damp environment in the wall, this initially reacts to form hydrogen chloride and then an aqueous hydrochloric acid that reacts with the sodium hydroxide also present in the wall to form water and salt (sodium chloride). Due to this acid/base reaction, which also takes place between the applied lactic acid and the sodium hydroxide, heat is generated that has a thermal impact on the microorganisms and biofilms. In the presence of the acid that has now been applied, the chlorite formed in the second step is also converted into chlorine dioxide, thus causing the biofilms that are present to actively break up. The reaction of the hypochlorite with the hydrogen peroxide produces hydrogen chloride and involves an enormous amount of expansion that chemo-mechanically squeezes the organic material that has been killed and broken up out of the wall. This step is repeated as many times as required until no more mold appears on the area being treated and all of the chlorine from the second solution has been used up as a result.

In this step, all the organic material is removed, including the mycelium rooted in the wall. This means that even the mold stains or algae discoloration is also fully removed. Furthermore, this step neutralizes all substances from the previous steps and also pushes all of the residual substances from the previous solutions out of the wall, thus ensuring that no toxic or corrosive substances remain on the surface afterward. If there is a very large amount of organic material that escapes from the treated area, then it is possible that the applied liquids develop an insufficient wetting capacity. In this case, it would be necessary to mechanically wipe or wash it off as an intermediate step in order to remove the organic material from the surface before the next step of the method.

The fourth solution is then applied in order to shrink or close the wall's pores that have been opened, and therefore avoid decontamination from a new mold infestation as far as possible. In addition, the quaternary ammonium compounds contained in the fourth solution act as a toxicologically harmless disinfectant. The following compound groups may be considered as possible quaternary ammonium compounds to be used in the fourth solution: alkyltrimethylammonium salts, dialkyl dimethyl ammonium salts, benzalkonium salts, esterquats, ethoxylated quaternary ammonium compounds, alkaloid sanguinarine.

Another feature of the invention is that the first solution is aqueous and contains at least sodium alkane sulfonate with a concentration of 1-5%, alcohol ethoxylate with a concentration of 1-5%, butyldiglycol with a concentration of 5-15% and pentapotassium triphosphate with a concentration of 1-5%. The addition of alcohol in the first solution causes the mycelium branches to shrink, which causes the pores to open even wider. All of the percentages stated in the description and the claims are meant as weight percent.

According to another feature of the invention, the second solution is aqueous and contains at least sodium hydroxide with a concentration of 5-15% and sodium hypochlorite with a concentration of 1-10%. Instead of hypochlorite, another suitable halide compound can of course also be used in a similar way. In many known methods, only one treatment using hypochlorite takes place, which causes the mold to be removed from the surface but does not reach the mycelium branches deeper within the masonry, meaning that it is possible for the mold to grow back very quickly. In the case presented here, the second solution penetrates deeply and therefore completely destroys the infestation. Depending on the material of the affected surface and the depth of penetration associated with it, the second solution can also be applied several times.

Another feature of the invention is that the third solution is aqueous and contains at least hydrogen peroxide with a concentration of 1-5%, polyaminopropyl biguanide with a concentration of up to 1% and lactic acid with a concentration of 1-5%. Instead of lactic acid, other acids can of course also be used. In this reaction step, a severe amount of mold is formed on the surface being treated, so the treatment is continued until this foaming ends. All organic material that has been killed is flushed out of the wall's pores and the pH value within the masonry is reneutralized.

Another feature of the invention is that the fourth solution is aqueous and contains at least benzalkonium chloride with a concentration of 5-15% and ethylenediaminetetraacetate with a concentration of 1%. The fourth solution acts as a sealant for the treated surface and has a high level of persistence in the masonry, however it can biodegrade slightly in floors. It is also harmless to humans and can therefore also be used with no fear of harm in living spaces and eating areas.

According to another feature of the invention, it is ensured that, in the final step of the method when using it on surfaces in an internal room, the third solution is misted into the air of the room. This mist treatment may constitute a final disinfection of the environment in internal rooms, and the substances in the third solution are also easily biodegradable or decompose after a short period of time and do not pose any danger to humans.

Finally, another feature of the invention is that each solution is applied to the surface by spraying. In principle, the solutions can be applied to the affected area using other methods, such as painting, sprinkling, pouring, etc. However, the preferred method is for each solution to be sprayed on, as this means that the amount of solution used is very low and enables it to be applied evenly across the affected areas.

The inventive method is also suitable for plastic bonded exterior plasters, such as those used on the outside walls of thermally insulated houses. Here, the treatment can also be terminated after the third step of the method because the plastic reacts differently and the pores do not need to be treated any further. In this case, it is sufficient to rinse the wall with water in order to remove the biological residue of the growth.

WAYS FOR CARRYING OUT THE INVENTION

An embodiment of the inventive method and the solutions used within it is described below.

A wall surface of about 5 $m^2$ infested with mold was treated with the inventive method using the solutions indicated below.

250 ml of the first solution was sprayed onto the wall.
1 l of the first solution contained:
125 g Sodium alkane sulfonate
125 g alcohol ethoxylate
375 g butyldiglycol
125 g pentapotassium triphosphate After a treatment time of 15 minutes, the second solution was applied. Based on the masonry (solid brick wall in an old building, plastered and painted white) the second solution was sprayed on 3 times. A total amount of 2 l was used.
1 l of the second solution contained:
300 g sodium hydroxide
200 g sodium hypochlorite After a treatment time of 30 minutes, the third solution was sprayed onto the wall twice. A total amount of 2 l was used.
1 l of the third solution contained:
100 g hydrogen peroxide
10 g polyaminopropyl biguanide
100 g/ml lactic acid After the final treatment stage, absolutely no foaming could be observed.

Finally, the fourth solution was sprayed onto the wall. A total amount of 500 ml was used.
1 l of the fourth solution contained:
0.75 g benzalkonium chloride
0.05 g ethylenediaminetetraacetate Finally, 250 ml of the third solution was atomized in a nebulizer (N80101240 Pfalz Technik AUTOMATIC W03, S-B10.W03 DD; Throughput 2.5-3 bar: 2-7 l/min effective; generated aerosol particles size about 8μ) for 5 minutes in the room in which the treated surface was located. After about 160 minutes the procedure was completed and the room could be used safely.

Since the wall was previously obscured by a cabinet, the only cause of the mold build-up was deemed to be a lack of rear ventilation. Since now the wall is dry and the building is well drained, it can be assumed that the mold will not reappear within 3 years.

The invention claimed is:

1. A method of fighting mold, algae and other microorganisms on a porous surface of a wall, floor, ceiling or masonry, the method comprising the steps of sequentially:

applying to the surface a first solution that contains sodium alkane sultanate with a concentration of 1-5%, alcohol ethoxylate with a concentration of 1-5%, butyldiglycol with a concentration of 5-15%, and pentapotassium triphosphate with a concentration of 1-5% to open pores of the porous surface, thereafter applying to the surface to which the first solution was applied a second solution that has been made alkaline using sodium hydroxide and that contains sodium hypochlorite such that the second solution enters the pores of the surface opened by the first solution, thereafter applying to the surface to which the second solution has been applied a third solution that contains hydrogen peroxide and lactic acid as active substances that react with the second solution in the open pores so as to generate foam and continuing application of the third solution until foaming on the surface has ended, and thereafter applying to the surface to which the third solution has been applied a fourth solution that is aqueous and contains one quaternary ammonium compound to shrink or close the pores opened by the first solution.

2. The method according to claim 1, wherein the second solution is aqueous, the sodium hydroxide has a concentration of 5-15%, and the third solution further contains sodium hypochlorite with a concentration of 1-10%.

3. The method according to claim 1, wherein the third solution is aqueous, the hydrogen peroxide has a concentration of 1-5%, and the third solution further contains polyaminopropyl biguanide with a concentration of up to 1% and lactic acid with a concentration of 1-5%.

4. The method according to claim 1, wherein the fourth solution is aqueous and contains benzalkonium chloride at a concentration of 5-15% and ethylenediaminetetraacetate at a concentration of 1%.

5. The method according to claim 1, further comprising the step, subsequent to application of the fourth solution and when the surface is in an internal room, of:

spraying the third solution as a mist into the air of the room.

6. The method according to claim 1, wherein each of the solutions is applied by spraying onto the surface.

* * * * *